US011842800B2

(12) United States Patent
Das et al.

(10) Patent No.: US 11,842,800 B2
(45) Date of Patent: Dec. 12, 2023

(54) ARTIFICIAL INTELLIGENCE BASED TEMPERATURE MEASUREMENT IN MIXED FLUID CHAMBER

(71) Applicant: Tata Consultancy Services Limited, Mumbai (IN)

(72) Inventors: Rajat Kumar Das, Kolkata (IN); Arijit Sinharay, Kolkata (IN); Arijit Chowdhury, Kolkata (IN); Tapas Chakravarty, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 750 days.

(21) Appl. No.: 16/923,877

(22) Filed: Jul. 8, 2020

(65) Prior Publication Data

US 2021/0012863 A1   Jan. 14, 2021

(30) Foreign Application Priority Data

Jul. 9, 2019   (IN) .............................. 201921027506

(51) Int. Cl.
*G16C 60/00* (2019.01)
*G01K 1/02* (2021.01)
(Continued)

(52) U.S. Cl.
CPC .............. *G16C 60/00* (2019.02); *G01K 1/026* (2013.01); *G01K 7/02* (2013.01); *G01K 11/24* (2013.01)

(58) Field of Classification Search
CPC .......... G16C 60/00; G01K 1/026; G01K 7/02; G01K 11/24
See application file for complete search history.

(56) References Cited

U.S. PATENT DOCUMENTS

2002/0105999 A1\* 8/2002 Wallen .................. G01K 11/24
374/117

FOREIGN PATENT DOCUMENTS

CN   101457268 B   8/2010
CN   108981952 A   12/2018
(Continued)

OTHER PUBLICATIONS

Ali et al., Artificial Intelligence techniques applied as estimator in chemical process systems—A literature survey, 2015, Elsevier, Expert Systems with Applications, 42, 5915-5931. (Year: 2015).\*
(Continued)

*Primary Examiner* — Jennifer Wecker
*Assistant Examiner* — Kathryn Elizabeth Limbaugh
(74) *Attorney, Agent, or Firm* — Finnegan, Henderson, Farabow, Garrett & Dunner LLP

(57) ABSTRACT

Temperature measurement is an important part of many potential applications in process industry. Conventional temperature measurement methods require manual intervention for process monitoring and fail to provide accurate and precise measurement of temperature of an enclosed mixed fluid chamber. The present disclosure provides artificial intelligence based temperature measurement in mixed fluid chamber. A plurality of inputs pertaining to the mixed fluid chamber are received to build a fluid based model. The fluid based model is used to generate one or more fluid parameters. The one or more fluid parameters are used along with a ground truth temperature data and the received plurality of inputs for training an artificial intelligence (AI) based model. However, the AI based model is trained with and without knowledge of fluid flow. The trained AI based model is further used to accurately estimate temperature of the mixed fluid chamber for a plurality of test input data.

15 Claims, 5 Drawing Sheets

(51) Int. Cl.
  *G01K 7/02* (2021.01)
  *G01K 11/24* (2006.01)

(56) References Cited

FOREIGN PATENT DOCUMENTS

TW          201530277          5/2016
WO    WO2000050890 A1    8/2000

OTHER PUBLICATIONS

R. Dhanuskodi et al., (2015), "Artificial Neural Networks Model for Predicting Wall Temperature of Supercritical Boilers," *Applied Thermal Engineering*, retrieved from https://www.researchgate.net/publication/282638830_Artificial_Neural_Networks_model_for_predicting_wall_temperature_of_supercritical_boilers/link/59152dab0f7e9b70f9c4602/download.

* cited by examiner

ARTIFICIAL INTELLIGENCE BASED TEMPERATURE MEASUREMENT IN MIXED FLUID CHAMBER

PRIORITY CLAIM

This U.S. patent application claims priority under 35 U.S.C. § 119 to: India Application No. 201921027506, filed on Jul. 9, 2019. The entire contents of the aforementioned application are incorporated herein by reference.

TECHNICAL FIELD

The disclosure herein generally relates to field of temperature measurement, more particularly, to artificial intelligence based temperature measurement in mixed fluid chamber.

BACKGROUND

Quality standard in process control industries utilizing enclosed fluid chambers such as foundry, industrial boiler, glass/ceramic manufacturing plants, chemical process, is an important parameter. It is observed that better process control such as maintaining optimal temperature of mixed fluid chamber improves product quality, and further reduces emission of gases. To improve the process control, non-contact based temperature measurement systems are used which help in preventing hotspots and thermal shocks to ensure worker and plant safety. However, continuous mixed fluid temperature measurement using non-contact systems is a prevalent problem in different process industries.

Conventional methods utilize thermocouples and other conventional instruments for measuring temperature of the mixed fluid chamber. However, the thermocouples and the other conventional instruments fail to meet industry demands. Moreover, the conventional instruments often require manual interventions and suffer from accuracy and response time.

SUMMARY

Embodiments of the present disclosure present technological improvements as solutions to one or more of the above-mentioned technical problems recognized by the inventors in conventional systems. For example, in one embodiment, a method for artificial intelligence based temperature measurement in mixed fluid chamber is provided. The method comprising receiving, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber. In an embodiment, a plurality of acoustic transmitter and receiver pairs are used in the mixed fluid chamber to provide the sound velocity information determined using the acoustic pyrometer based technique. In an embodiment, inherent drift and noise is reduced by using the plurality of acoustic transmitter and receiver pairs. In an embodiment, the method further comprising determining, one or more fluid parameters using one of (i) a bernoulli principle based fluid model or (ii) a state space based fluid model. In an embodiment, the one or more fluid parameters determined using the bernoulli principle based fluid model include spatio-temporal variation in concentration of the one or more fluids present in close proximity of the one or more chemical sensors in the mixed fluid chamber. In an embodiment, the state space based fluid model is implemented using a Kalman filter or an extended Kalman filter. In an embodiment, the method further comprising determining, an information pertaining to a plurality of thermocouples comprised in the mixed fluid chamber, wherein the information includes corresponding location coordinates of the plurality of thermocouples and temperature measured at the corresponding location coordinates of the plurality of thermocouples; generating, ground truth temperature data for the mixed fluid chamber using a gradient based heat diffusion model based on the information pertaining to each of the plurality of thermocouples; training an artificial intelligence (AI) based model using the one or more fluid parameters, the generated ground truth temperature data, and the sound velocity information; and estimating, for a plurality of test input data, temperature of the mixed fluid chamber using the trained AI based model. In an embodiment, the ground truth temperature data is indicative of spatio-temporal variation of temperature of the one or more fluids inside the mixed fluid chamber. In an embodiment, the method further comprising training the artificial intelligence (AI) based model to function as a stand-alone model without using the one or more fluid parameters determined by the bernoulli principle based fluid model or the state space based fluid model.

In another embodiment, a system for artificial intelligence based temperature measurement in mixed fluid chamber is provided. The system comprising a memory; one or more communication interfaces; and one or more hardware processors coupled to said memory through said one or more communication interfaces, wherein said one or more hardware processors are configured to: receive, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber. In an embodiment, a plurality of acoustic transmitter and receiver pairs are used in the mixed fluid chamber to provide the sound velocity information determined using the acoustic pyrometer based technique. In an embodiment, inherent drift and noise is reduced by using the plurality of acoustic transmitter and receiver pairs. In an embodiment, the one or more hardware processors are further configured to determine, one or more fluid parameters using one of (i) a bernoulli principle based fluid model or (ii) a state space based fluid model. In an embodiment, the one or more fluid parameters determined using the bernoulli principle based fluid model include spatio-temporal variation in concentration of the one or more fluids present in close proximity of the one or more chemical sensors in the mixed fluid chamber. In an embodiment, the state space based fluid model is implemented using a Kalman filter or an extended Kalman filter. In an embodiment, the one or more hardware processors are further configured to determine, an information pertaining to a plurality of thermocouples comprised in the mixed fluid chamber, wherein the information includes corresponding location coordinates of the plurality of thermocouples and temperature measured at the corresponding location coordinates of the plurality of thermocouples; generate, ground truth temperature data for the mixed fluid chamber using a gradient based heat diffusion model based on the information pertaining to each of the plurality of thermocouples; train an artificial intelligence (AI) based model using the one or more fluid parameters, the generated ground truth temperature data, and the sound velocity information; and estimate, for a plurality of test input data, temperature of the mixed fluid chamber using the trained AI based model. In an embodiment, the ground truth temperature data is indicative of spatio-temporal variation of temperature of the one or more fluids inside the mixed fluid chamber. In an embodiment, the one or more hardware processors are further configured to train the artificial intelligence (AI) based model to function as a stand-alone model without using the one or more fluid parameters determined by the bernoulli principle based fluid model or the state space based fluid model.

In yet another embodiment, one or more non-transitory computer readable mediums for artificial intelligence based temperature measurement in mixed fluid chamber is provided. The one or more non-transitory computer readable mediums comprising one or more instructions which when executed by one or more hardware processors cause receiving, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber. In an embodiment, a plurality of acoustic transmitter and receiver pairs are used in the mixed fluid chamber to provide the sound velocity information determined using the acoustic pyrometer based technique. In an embodiment, inherent drift and noise is reduced by using the plurality of acoustic transmitter and receiver pairs. In an embodiment, the instructions may further cause determining, one or more fluid parameters using one of (i) a bernoulli principle based fluid model or (ii) a state space based fluid model. In an embodiment, the one or more fluid parameters determined using the bernoulli principle based fluid model include spatio-temporal variation in concentration of the one or more fluids present in close proximity of the one or more chemical sensors in the mixed fluid chamber. In an embodiment, the state space based fluid model is implemented using a Kalman filter or an extended Kalman filter. In an embodiment, the instructions may further cause determining, an information pertaining to a plurality of thermocouples comprised in the mixed fluid chamber, wherein the information includes corresponding location coordinates of the plurality of thermocouples and temperature measured at the corresponding location coordinates of the plurality of thermocouples; generating, ground truth temperature data for the mixed fluid chamber using a gradient based heat diffusion model based on the information pertaining to each of the plurality of thermocouples; training an artificial intelligence (AI) based model using the one or more fluid parameters, the generated ground truth temperature data, and the sound velocity information; and estimating, for a plurality of test input data, temperature of the mixed fluid chamber using the trained AI based model. In an embodiment, the ground truth temperature data is indicative of spatio-temporal variation of temperature of the one or more fluids inside the mixed fluid chamber. In an embodiment, the instructions may further cause training the artificial intelligence (AI) based model to function as a stand-alone model without using the one or more fluid parameters determined by the bernoulli principle based fluid model or the state space based fluid model.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
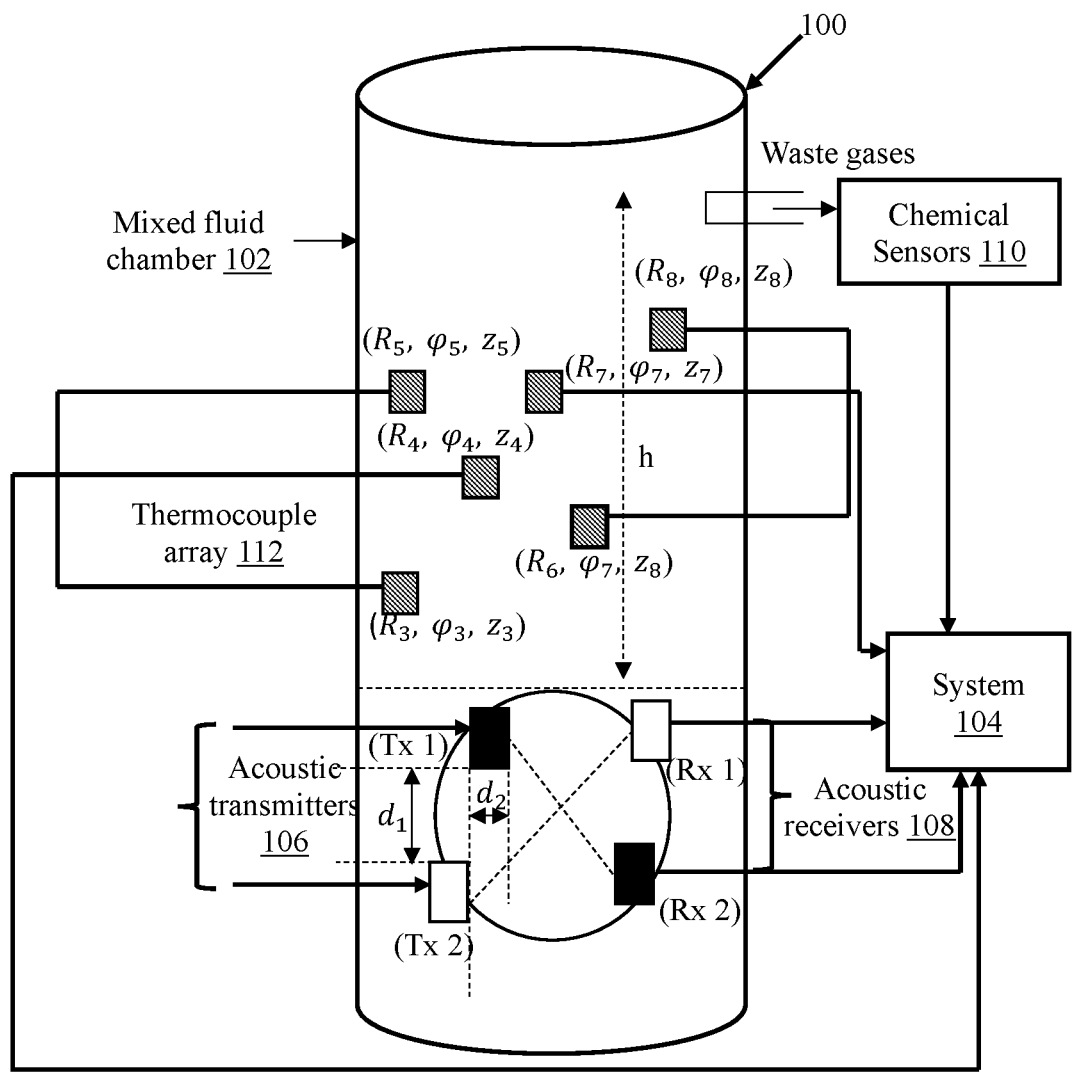
FIG. 1 illustrates an exemplary chamber environment with a system for implementing artificial intelligence based temperature measurement in mixed fluid chamber, in accordance with an embodiment of present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein provide artificial intelligence based temperature measurement in mixed fluid chamber. The typical interpretation of results obtained from conventional temperature measurement methods has been modified to solve a problem of accurately measuring temperature of fluid within an enclosed chamber that contains mixture of different compositions. The utilization of artificial intelligence helps in continuous monitoring of temperature of mixed fluid chamber by providing continuous feedback for process monitoring. The method of the present disclosure describes artificial intelligence based temperature measurement in mixed fluid chamber. In the method of present disclosure, an average temperature is measured based on training of an artificial intelligence based model with a plurality of inputs pertaining to the mixed fluid chamber, wherein the plurality of inputs include sound velocity information determined using an acoustic pyrometer based technique, information acquired by one or more chemical sensors deployed in the mixed fluid chamber such as concentration of one or more fluids and location information of the one or more chemical sensors, dimension of the mixed fluid chamber, and location and temperature measurements of a plurality of thermocouples placed in the mixed fluid chamber.

Referring now to the drawings, and more particularly to FIG. 1 through FIG. 5, where similar reference characters denote corresponding features consistently throughout the figures, there are shown preferred embodiments and these embodiments are described in the context of the following exemplary system and/or method.

FIG. 1 illustrates an exemplary chamber environment 100 with a system 104 for implementing artificial intelligence based temperature measurement in a mixed fluid chamber, in accordance with an embodiment of present disclosure. The chamber environment 100 utilizes a plurality of acoustic transmitters 106, a plurality of acoustic receivers 108, a thermocouple array 112 comprising a plurality of thermocouples placed at different locations near wall of the mixed fluid chamber 102, and one or more chemical sensors 110 in the mixed fluid chamber 102 for measuring temperature of the mixed fluid chamber 102 using artificial intelligence based technique(s)/model(s).

In an embodiment, the plurality of acoustic transmitters 106, the plurality of acoustic receivers 108, the thermocouple array 112, and the one or more chemical sensors 110 mounted in the mixed fluid chamber 102 may reside in the system 104 and/or may act as standalone unit. The system 104 is configured to process and analyze the data received from the plurality of acoustic transmitters 106, the plurality of acoustic receivers 108, the thermocouple array 112, and the one or more chemical sensors 110 for artificial intelligence based temperature measurement in the mixed fluid chamber 102. The system 104 is configured to process and analyze the received data in accordance with a plurality of models, further explained in conjunction with FIG. 2 and FIG. 3.

Figure 2:
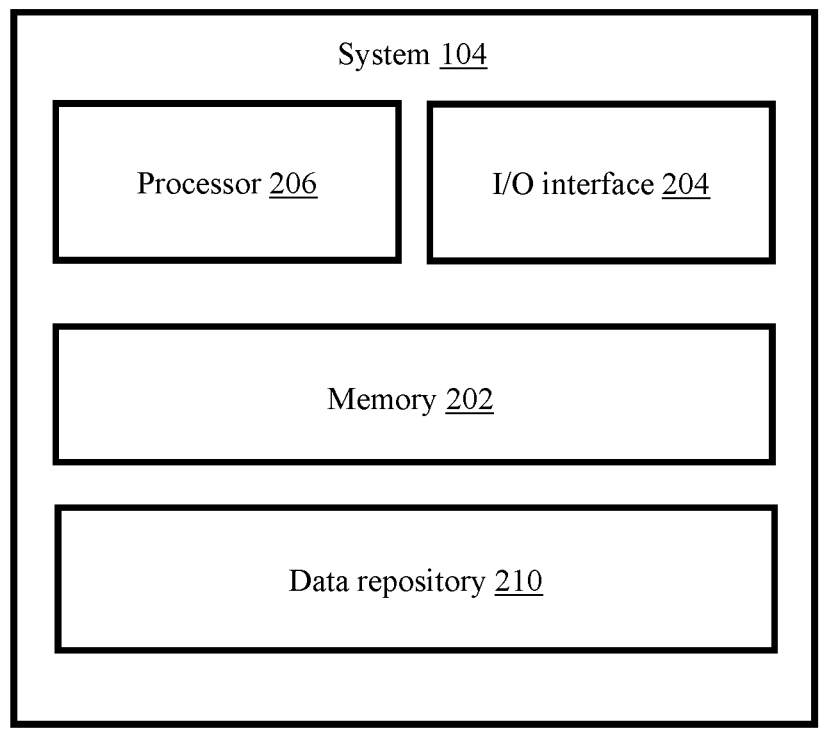
FIG. 2 illustrates a block diagram of the system of FIG. 1 for artificial intelligence based temperature measurement in mixed fluid chamber, according to some embodiments of the present disclosure.

FIG. 2 illustrates a block diagram of the system 104 of FIG. 1 for artificial intelligence based temperature measurement in the mixed fluid chamber 102 of FIG. 1, according to some embodiments of the present disclosure.

In an embodiment, the system 104 includes or is otherwise in communication with one or more hardware processors such as a processor 206, an Input/Output interface 204, and at least one memory such as a memory 202. The processor 206, the I/O interface 204, and the memory 202, may be coupled by a system bus (not shown in FIG. 2).

The I/O interface 204 may include a variety of software and hardware interfaces, for example, a web interface, a graphical user interface, and the like. The interfaces 204 may include a variety of software and hardware interfaces, for example, interfaces for peripheral device(s), such as a keyboard, a mouse, an external memory, a camera device, and a printer. The interfaces 204 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 204 may include one or more ports for connecting a number of computing systems with one another or to another server computer. The I/O interface 204 may include one or more ports for connecting a number of devices to one another or to another server.

The hardware processor 206 may be implemented as one or more microprocessors, microcomputers, microcontrollers, digital signal processors, central processing units, state machines, combinational circuits, application specific integrated circuits, semiconductor devices, logic circuitries including switches, and/or any devices that manipulate signals based on operational instructions. Among other capabilities, the hardware processor 206 is configured to fetch and execute computer-readable instructions stored in the memory 202.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 202 includes a data repository 210 for storing data processed, received, and generated as output(s) by the system 104. The memory 202 stores a plurality of models such as fluid models and artificial intelligence based models which are further used for temperature measurement in the mixed fluid chamber 102. The plurality of models stored in the memory 202 may include routines, programs, objects, components, data structures, and so on, which perform particular tasks or implement particular (abstract) data types.

The data repository 210, amongst other things, includes a system data base a nd other data. The other data may include data received for training the plurality of models and data generated as a result of the execution of the plurality of models stored in the memory 202. The training data may be further learnt to provide improved learning of the models in the next iterations to output desired results with improved accuracy.

Figure 3:
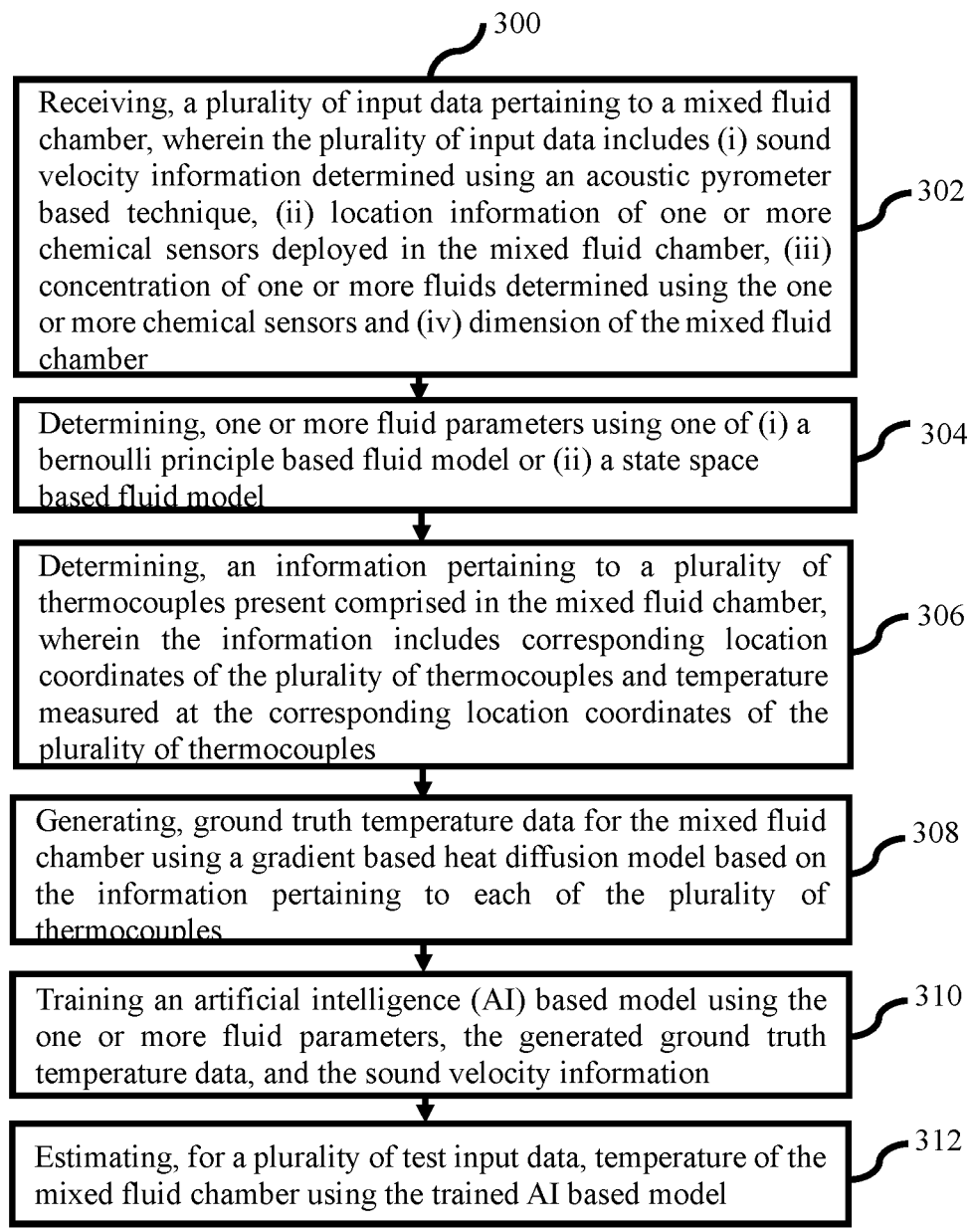
FIG. 3 illustrates an exemplary flow diagram of a processor implemented method for artificial intelligence based temperature measurement in mixed fluid chamber, in accordance with some embodiments of the present disclosure.
Figure 4:
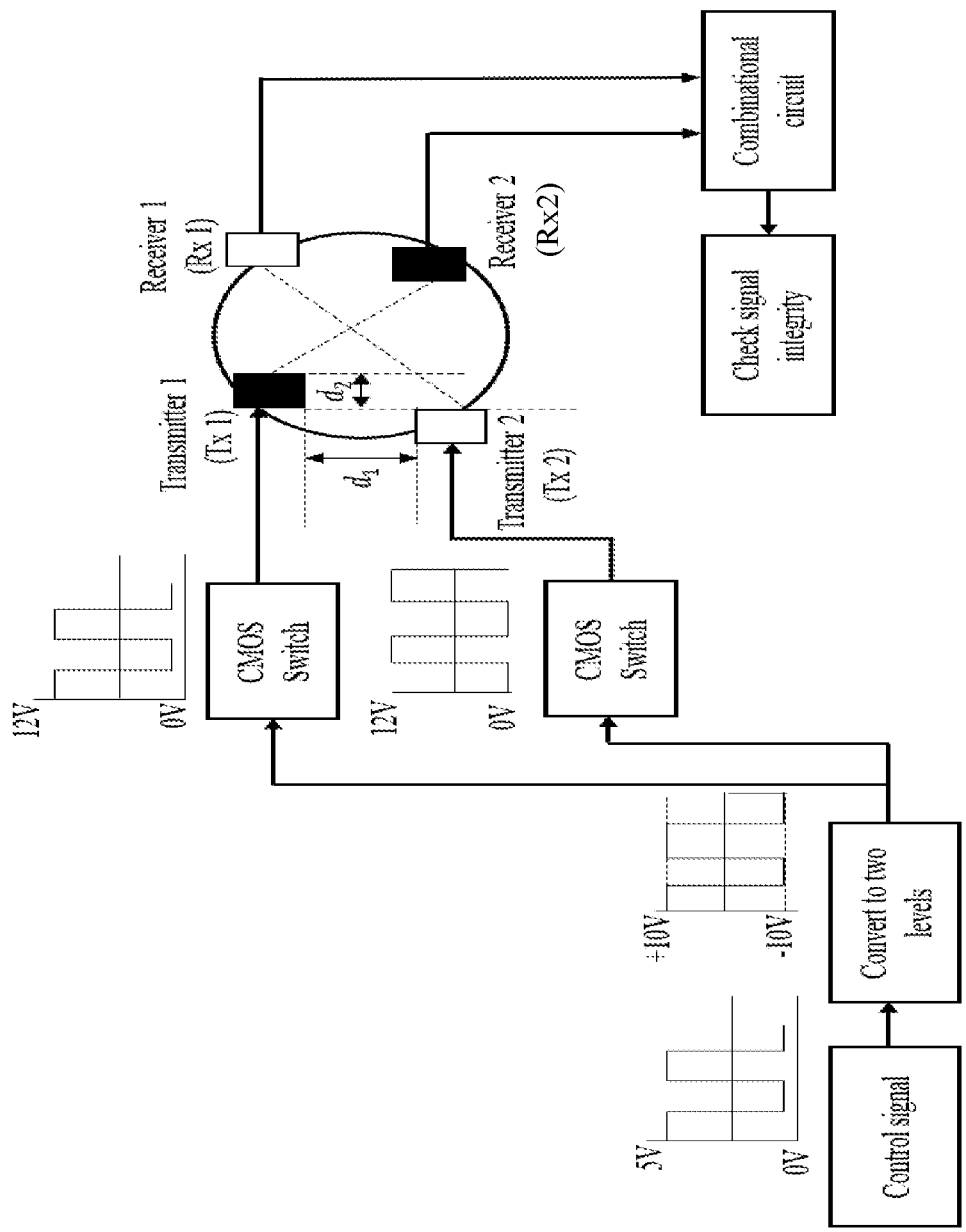
FIG. 4 illustrates a functional diagram depicting acoustic pyrometer based measurement of sound velocity for artificial intelligence based temperature measurement in the mixed fluid chamber, in accordance with some embodiments of the present disclosure.

In an embodiment, the one or more hardware processors 206 can be configured to perform artificial intelligence based temperature measurement in the mixed fluid chamber which can be carried out by using methodology, described in conjunction with FIG. 3, FIG. 4, and use case examples.

FIG. 3, illustrate an exemplary flow diagram of a processor implemented method 300, implemented by the system 104 of FIG. 1 and FIG. 2 for artificial intelligence based temperature measurement in the mixed fluid chamber, in accordance with some embodiments of the present disclosure. Referring to FIG. 3, at step 302 of the present disclosure, the one or more hardware processors 206 receive a plurality of input data pertaining to the mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber.

In an embodiment, the dimension of the mixed fluid chamber (say D) may be 10 meters. In an embodiment, the sound velocity information is determined using an acoustic pyrometer technique based measurement. The acoustic pyrometer technique based measurement is based on a principle that sound speed through a medium is related to temperature of the medium. Here an acoustic transmitter and receiver is used to measure the temperature of the medium.

In other words, this is an indirect way of measuring temperature, where sound velocity is first determined and then by correlating with the medium the temperature is mapped. In an embodiment, to determine the sound velocity, the acoustic transmitter is first excited with an excitation signal which results in formation of a standing wave. Further, one or more features of the standing wave are analyzed to provide sound velocity. In an embodiment, range of the value of sound velocity determined using an acoustic pyrometer technique based measurement could be 570 meter/sec to 1130 meter/sec. FIG. 4 illustrates a functional diagram depicting acoustic pyrometer technique based measurement of sound velocity for artificial intelligence based temperature measurement in the mixed fluid chamber 102, in accordance with some embodiments of the present disclosure. As can be seen in FIG. 4, a plurality of acoustic transmitter and receiver pairs (two pairs are used in FIG. 4 for the ease of representation) are used in the mixed fluid chamber 102 to provide the sound velocity information. Here, the acoustic transmitter and receiver pairs are spatially separated according to a transmitter beam-width to avoid any interference with each other and are controlled by a square wave of 50% duty cycle. It can be seen in FIG. 1 that the acoustic transmitters 106 are placed in such a way that acoustic transmitter 1 (say Tx1) is at a distance '$d_1$' from acoustic transmitter 2 (say Tx2) horizontally and at a distance '$d_2$' vertically. In a similar way, acoustic receiver 1 (say Rx1) is placed at a distance '$d_1$' from acoustic receiver 2 (say Rx 2) horizontally and at a distance '$d_2$' vertically. Here, value of '$d_1$' may be 1 meter and value of '$d_2$' is determined based on a relationship with wavelength of the excitation signal ($\lambda$) such that $d_2=2/n\lambda$. Here, the value of is 8 mm. Triggering of the square wave of 50% duty cycle to control the acoustic transmitter and receiver pairs ensures that only one acoustic transmitter and receiver pair (either Tx1-Rx1 or Tx2-Rx2) gets activated for a given time. As can be seen in FIG. 4, a CMOS switch is used before each acoustic transmitter. The output of these CMOS switches will be complementary binary logic so that at any time instant, only one acoustic transmitter is switched on and other is in off condition. Thus, at any instant, output is received from any one of the acoustic receiver. Further, combinational circuit helps in stitching outputs received from all the acoustic receivers. The output of acoustic receivers (here output of Rx1 and Rx2) is compared to check signal integrity. Further, if a difference is detected in the average signal level between two acoustic receivers, then the particular acoustic receiver output is dropped. The difference in the average signal level may be detected due to any abrupt change inside the mixed fluid chamber 102. Further, output of the Tx-Rx pairs is used to calculate an average sound velocity in the mixed fluid chamber. For example, at a given time instant, only one Tx-Rx pair is activated providing the corresponding average sound velocity. In an embodiment, the acoustic transmitter may be but is not limited to a speaker and the acoustic receiver may be but is not limited to a microphone. In an embodiment, as shown in FIG. 1, location of acoustic transmitter and receiver are represented by cylindrical coordinates. For example, location coordinates of the acoustic transmitter may be ($r_1$, 0°, 0.5) and location coordinates of acoustic receiver may be ($r_2$, 15°, 0.5). In an embodiment, use of the plurality of acoustic transmitter and acoustic receiver pairs helps in reducing sensor inherent drift and noise. Here both the acoustic transmitters are switched on and off simultaneously. In comparison to continuous excitation, on-off based excitation reduce the sensor inherent drift. Further, output received from multiple transmitter receiver pairs helps in reducing the noise (e.g., environmental noise). In an embodiment, the one or more chemical sensors are located near exit point of fluid at a pre-defined height (say h as shown in FIG. 1) from the plurality of acoustic transmitters 106 and the plurality of acoustic receivers 108 in the mixed fluid chamber 102. In an embodiment, the predefined height (h) may be 30 meters. In an embodiment, the concentration of one or more fluids (say $f_1$, $f_2$, $f_3$, and $f_4$) may be 0.3%, 0.4%, 0.2%, 0.1% respectively which must be summed to unity. In an embodiment, range of the sound velocity measured using the acoustic pyrometer based technique may be in a range, but is not limited to, 570 meter/sec to 1130 meter/sec.

Further, as depicted in step 304 of FIG. 3, the one or more hardware processors 206 determine one or more fluid parameters using one of (i) a Bernoulli principle based fluid model or (ii) a state s pace based fluid model. As is known in the art that the acoustic pyrometer based temperature measurement is based on a principle that the sound velocity information through a medium is related to the temperature of the medium. Thus, for accurate measurement of temperature, the concentration of different fluids needs to be known at the sound velocity measurement location (near to the plurality of acoustic transmitter and receiver pairs). However, using the one or more chemical sensors, the concentration of the one or more fluids is measured at a height difference (same as the pre-defined height h) from the actual sound speed measurement point as shown in FIG. 1. Here, the concentration of the one or more fluids (alternatively referred as fluid density) measured by the one or more chemical sensors at the predefined heighth is represented by ρ.

In an embodiment, it is evident from FIG. 1 that the one or more chemical sensors are placed near the fluid exit point which is narrower compared to the actual mixed fluid chamber. Therefore, fluids are required to speed up when they reach a narrow constricted section in order to maintain a constant volume flow rate as shown in equation (1) mentioned below as:

$$v_i A_i = \text{volume flow rate} = \text{constant} \quad (1)$$

Here, $v_i$ refers to fluid velocity and $A_i$ refers to cross sectional area of the mixed fluid chamber. Thus, a fluid model is required to model the fluid flow characterized in equation (1) to estimate concentration of the one or more fluids present near the sound velocity measurement point. In an embodiment, the one or more fluid parameters determined using the bernoulli principle based fluid model include spatio-temporal variation in concentration of the one or more fluids present near the one or more chemical sensors in the mixed fluid chamber. The concentration of the one or more fluids present near the sound velocity measurement point is represented by p*. In an embodiment, the bernoulli principle based fluid model relates one or more fluid parameters such as pressure, velocity, and height of any two points (e.g., say point 1 and point 2) in a flowing fluid of density ρ and ρ* in accordance with equation (2) shown below as:

$$\tfrac{1}{2}v_1^2 + \rho^* g h_1 + P_{out} = \tfrac{1}{2}\rho v_2^2 + \mu g h_2 + P_{in} \quad (2)$$

Here, $P_{out}$, $v_1$, $h_1$ refer to the pressure, the velocity, and the height of the fluid at point 1 and $P_{in}$, $v_2$, $h_2$ refer to the pressure, the velocity, and the height of the fluid at point 2 respectively.

In another embodiment, the location information of the one or more chemical sensors deployed in the mixed fluid chamber, concentration of the one or more fluids determined using the one or more chemical sensors near the exit point of the mixed fluid chamber and the dimension of the mixed fluid chamber are provided as input to the bernoulli principle based fluid model. Further, point 1 and point 2 mentioned in equation (2) can be referred as the and sound velocity measurement location and location of the one or more chemical sensors near the exit point respectively. Further, using equation (1), the velocity at point 2 ($v_2$) can be derived as shown in equation (3) below as:

$$v_2 = \frac{v_1 A_1}{A_2} \quad (3)$$

Here, $A_1$ refers to area of cross section of the mixed fluid chamber at point 1 and $A_2$ refers to area of cross section of the mixed fluid chamber at point 2 which is exit point of the mixed fluid chamber, wherein $A_2$ is replaced by dimensions of the mixed fluid chamber (D) as shown in equation (4) below as:

$$A_2 = \frac{\pi D^2}{4} \quad (4)$$

Further, the concentration of the one or more fluids present near the sound velocity measurement point $\rho^*$ is obtained by substituting $h_1=0$, $h_2=h$ and putting values of $v_2$ and $A_2$ from equation (3) and equation (4) into equation (2). Upon obtaining the concentration of the one or more fluids present near the sound velocity measurement point, time required (T) for fluid to flow from the point 1 to point 2 is determined.

In an embodiment, based on bernoulli principle based fluid flow model, a time delayed version of acoustic pyrometer based sound velocity information is mapped with current value of the concentration of the one or more fluids present near the exit point at time 't' which is shown in equation 5 below as:

$$V_{sound}(t-T) \rightarrow c(t) \quad (5)$$

Here, $V_{sound}$ (t–T) denotes the time delayed version of acoustic pyrometer based sound velocity information and c(t) denotes the current value of the concentration of the one or more fluids present near the exit point at time t. Table 1 provides a visualization of the above-mentioned mapping.

TABLE 1

| $V_{sound}$ (t – T) | c(t) |
|---|---|
| $V_1$ | $C_1$ |
| $V_2$ | Nan |
| Nan | $C_2$ |
| $V_3$ | $C_3$ |
| $V_4$ | $C_4$ |
| Nan | Nan |

It can be seen from Table 1 that during time synchronized mapping of acoustic pyrometer based sound velocity information and c(t), some values are identified as missing values represented as Nan in Table 1. This may occur due to clocking mismatch between the one or more chemical sensors and the acoustic pyrometer. The missing values can be filled using an interpolation method namely a spline function or standard cubic spline method. The interpolation is a standard technique where the spline based function takes previous values as input and determine the missing point values.

In an embodiment, there exists a possibility of improper characterization of different attributes of the fluid flow inside the chamber by the bernoullli principle based fluid flow model. These attributes may include but are not limited to unknown mixture of chemicals in non-homogenous way and non-laminar flow of fluid. In such cases, the state space based fluid model is used to determine the one or more fluid parameters. In an embodiment, the state space based fluid model is implemented using a Kalman filter or an Extended Kalman filter. In an embodiment, the sound velocity information determined using the acoustic pyrometer based technique, the location information of the one or more chemical sensors deployed in the mixed fluid chamber, concentration of the one or more fluids determined using the one or more chemical sensors near the exit point of the mixed fluid chamber and the dimension of the mixed fluid chamber are provided as input to the state space based fluid model. In an embodiment, the one or more fluid parameters determined using the state space based fluid model include a state transition model, process noise, a covariance matrix of observation noise ($\varepsilon$) and an observation model, wherein the observation model maps a true state space into an observed space. For example, it is assumed that measured density depicting concentration of the one or more fluids near the exit point of the mixed fluid chamber is denoted by $P_t$ and density depicting concentration of the one or more fluids at the sound velocity measurement location is denoted by $P^*$. Then, $P^*$ is determined using equation (6) and equation (7) which are representative of standard kalman filter based implementation provided below as:

$$P_t = F_t * P_{(t-1)} + e \quad (6)$$

Here, e is process noise with sum(e)=0 and $F_t$ is the state transition model $$P_t = A * P_t + v_t \quad (7)$$

Here A refers to the observation model and $v_t$ refers to the observation noise which is Gaussian in nature with zero mean. Similarly, e also represents a Gaussian noise with zero mean and independent. In an embodiment, initially both $F_t$ and A are identity matrix and over iterations the value of both $F_t$ and A may become as provided below $$F_t = \begin{bmatrix} 0.9 & 0.05 & 0 & 0 \\ 0.05 & 0.95 & 0.05 & 0 \\ 0.025 & 0 & 0.9 & 0.01 \\ 0.025 & 0 & 0.05 & 0.99 \end{bmatrix}, \text{ and}$$

$$A = \begin{bmatrix} 0.8 & 0.1 & 0 & 0.1 \\ 0.05 & 0.9 & 0.05 & 0 \\ 0.1 & 0 & 0.9 & 0 \\ 0.05 & 0 & 0.05 & 0.9 \end{bmatrix}$$

Further, the covariance matrix of observation noise ($\varepsilon$) is provided below $$\varepsilon = \begin{bmatrix} 0.05 \\ -0.025 \\ -0.025 \\ 0 \end{bmatrix}$$

Referring back to FIG. 3, at step 306, the one or more hardware processors determine an information pertaining to a plurality of thermocouples comprised in the mixed fluid chamber, wherein the information includes corresponding location coordinates of the plurality of thermocouples and temperature measured at the corresponding location coordinates of the plurality of thermocouples. To be protected from hostile environments, thermocouples are placed at closed proximity to the wall of the mixed fluid chamber and spatial temporal information of the thermocouple array is obtained by placing the plurality of thermocouples throughout the mixed fluid chamber at different known locations (e.g., locations with coordinates $(R_3, \varphi_3, z_3)$, $(R_4, \varphi_4, z_4)$, $(R_5, \varphi_5, z_5)$, $(R_6, \varphi_6, z_6)$, $(R_7, \varphi_7, z_7)$, and $(R_8, \varphi_8, z_8)$ as shown in FIG. 1). As can be seen in FIG. 1, location coordinates of thermocouples are provided in format of cylindrical coordinates (e.g., $(R, \varphi, z)$). For example, the location of thermocouple coordinates may be $(r, (0° C., 120° C., 240° C.), (2H/3±0.5 meter))$. In an embodiment, it is assumed that six thermocouples are placed in the mixed fluid chamber at six different locations and the temperature measured by the six thermocouples at their corresponding location are denoted by $T_1 \ldots T_6$.

Further, as depicted in step 308 of FIG. 3, the one or more hardware processors 206 generate ground truth temperature data for the mixed fluid chamber using a gradient based heat diffusion model based on the information pertaining to each of the plurality of thermocouples. In other words, upon determining the thermocouples data from different locations inside the mixed fluid chamber, ground truth data is generated in accordance with a 3D gradient based heat conduction equation in cylindrical coordinates. The 3D gradient based heat conduction equation in cylindrical coordinates is obtained from an energy balance on a volume element in cylindrical coordinates as shown in equation 8 below as:

$$\frac{1}{r}\frac{\partial}{\partial r}\left(k*r*\frac{\partial T}{\partial r}\right) + \frac{1}{r^2}\frac{\partial}{\partial \varphi}\left(k*r*\frac{\partial T}{\partial \varphi}\right) + \frac{\partial}{\partial z}\left(k\frac{\partial T}{\partial z}\right) + \dot{e} = \rho c \frac{\partial T}{\partial t} \quad (8)$$

Here, k denotes conductivity of the mixed fluid, $\dot{e}$ denotes rate at which energy is generated per unit volume of mixed fluid medium, $\rho$ denotes the density of the mixed fluid and c denotes the specific heat capacity of the mixed fluid. In the gradient based heat diffusion model as implemented by the present disclosure, there is no temperature variance in $\varphi$ direction so all $$\frac{d}{d\varphi}$$

terms in the equation (8) are zero. Further, boundary conditions are obtained from the thermocouples data and equation (8) is solved to generate the ground truth data. Here, boundary conditions are the dimension of the mixed fluid chamber and the location of the one or more chemical sensors. In an embodiment, the ground truth temperature data is indicative of spatio-temporal variation of the temperature $T(r, \varphi, z, t)$ of the one or more fluids inside the mixed fluid chamber.

Referring back to FIG. 3, at step 310, the one or more hardware processors 206 train an artificial intelligence (AI) based model using (i) the one or more fluid parameters, (ii) the generated ground truth temperature data, and (iii) the sound velocity information. In an embodiment, when the one or more fluid parameters are determined using the bernoulli principle based fluid model, then instead of training the AI based model, a statistical model is trained using the one or more fluid parameters along with the sound velocity information and the generated ground truth temperature data. The statistical models may include parametric non-linear regression model. Nonlinear regression is a statistical technique that helps in describing nonlinear relationships in data. The parametric non-linear regression model is used to model dependent variables (in this case, the concentration of the one or more fluids at the sound velocity measurement point and the sound velocity information) as a function of a combination of nonlinear parameters and one or more independent variables (in this case, the generated ground truth temperature data). Here, the ground truth temperature data refers to a reference point with which temperature values estimated by the trained model are compared. Here the temperature measured by each thermocouple is considered as ground truth temperature data which is compared with estimated temperature values to check the accuracy of the trained model. In an embodiment of the present disclosure, the parametric non-linear regression model may be uni-variate (single response variable) or multi-variate (multiple response variables). In an embodiment, the multivariate model refers to a model in which multiple response variables are modeled jointly. For example, a data consisting of heights and weights of children is collected over several years. Then, the multivariate model models the heights and weights jointly. However, the univariate model refers to a model which considers single response variable. For example, no information about the children's heights is required to the model their weights. The variables can take form of an exponential, trigonometric, power, or any other nonlinear function. To determine the nonlinear parameter estimates (in this case, the spatio-temporal variation of the temperature $T(r, \varphi, z, t)$), an iterative algorithm is used by the system of the present disclosure. Iterative algorithms are loop based repetitions of a process which use repetition structure. An infinite loop occurs with iteration if the loop-condition test never becomes false. Here, the spatio-temporal variation of the temperature is repeated in an iterative way till it matches with the ground truth temperature data.

Further, as depicted in step 312 of the FIG. 3, the one or more hardware processors 206 estimate temperature of the mixed fluid chamber using the trained AI based model for a plurality of test input data. The trained AI based model utilizes the ground truth temperature data as labeled data and predict the temperature of the mixed fluid chamber for unknown values of the one or fluid parameters.

Figure 5:
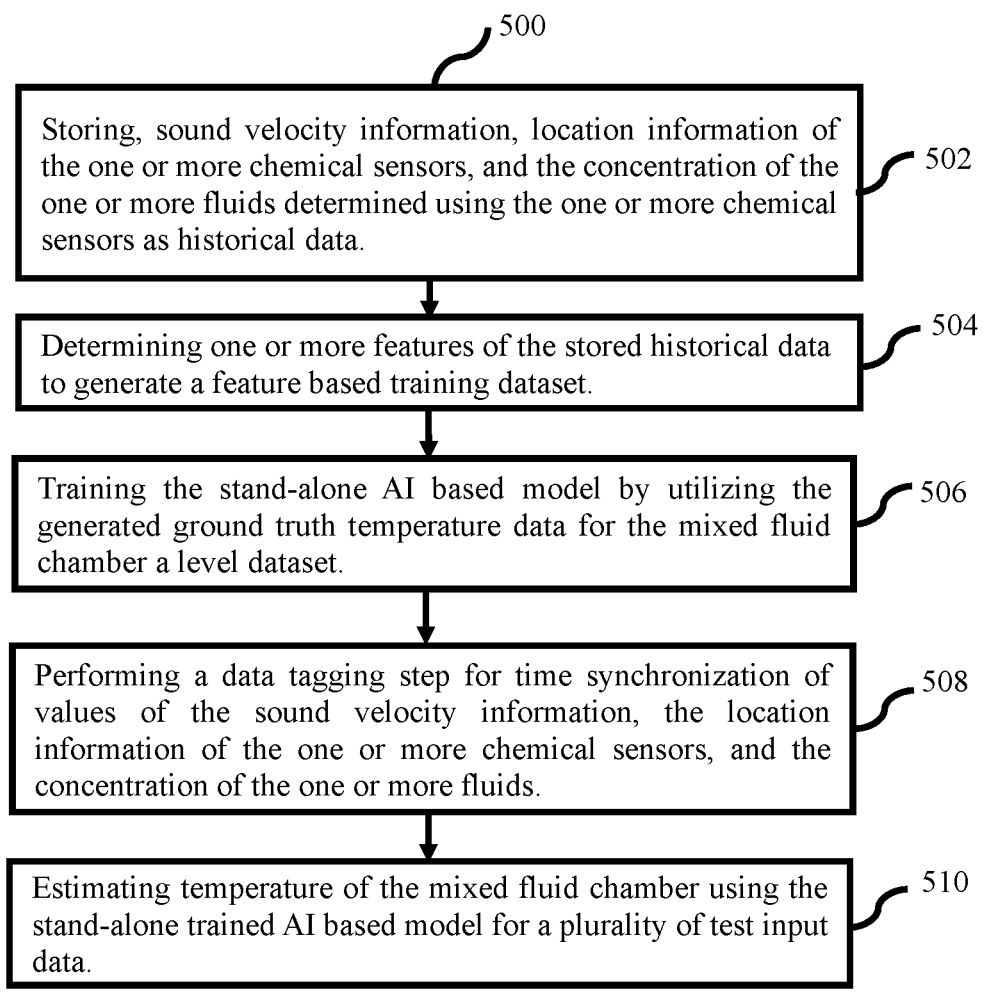
FIG. 5 illustrates an exemplary flow diagram of a stand-alone AI based model for temperature measurement in a mixed fluid chamber, in accordance with some embodiments of the present disclosure.

The one or more hardware processors 206 further train the artificial intelligence (AI) based model to function as a stand-alone model without using the one or more fluid parameters determined by the bernoulli principle based fluid model or the state space based fluid model. In an embodiment, when the parametric non-linear regression model which is trained based on the one or more fluid parameters determined using the bernoulli principle based fluid model may fail to accurately estimate the temperature of the mixed fluid chamber, then the AI based model which is trained based on the one or more fluid parameters determined using the state space based fluid model is used. Further, when the AI based model which is trained based on the one or more fluid parameters determined using the state space based fluid model also fails to accurately estimate the temperature of the mixed fluid chamber, then the artificial intelligence (AI) based model functions as a stand-alone model as shown in FIG. 5. In an embodiment, failure of the bernoulli principle based fluid model and state space based fluid model is determined by matching the temperature estimated by these models with the generated ground truth temperature data. FIG. 5 illustrates an exemplary flow diagram of the stand-alone AI based model for temperature measurement in the mixed fluid chamber, in accordance with some embodiments of the present disclosure. As can be seen in FIG. 5, at step 502, the sound velocity information and the concentration of the one or more fluids determined using the one or more chemical sensors are stored as historical data and provided as input to the stand-alone AI based model. Further, as depicted in step 504 of FIG. 5, one or more features of the stored historical data are determined to generate a feature based training dataset. In an embodiment, the historical data comprises raw values of the sound velocity information and the concentration of the one or more fluids determined using the one or more chemical sensors. For example $V_1, V_2, \ldots V_n$ represent the raw values of the sound velocity information, and $C_1, C_2, \ldots C_n$ represent the raw values of the concentration of the one or more fluids determined using the one or more chemical sensors. Then, the one or more features such as statistical features of the raw values are determined. The statistical features may include mean, variance, minima, maxima, entropy, kurtosis, skewness, and the like. Further, different combinations of these statistical features are used as the feature based training set to achieve maximum accuracy. For example, as a first combination, if the feature based training dataset comprises four statistical features including mean, variance, kurtosis, and entropy, then accuracy of the stand-alone AI model is determined using these features. However, if better accuracy is not obtained using above mentioned four statistical features, then a different combination of the statistical features is attempted. Further, as depicted in step 506, the generated ground truth temperature data for the mixed fluid chamber is used as a level dataset to train the stand-alone AI based model. In an embodiment, the stand-alone AI based model may be a regression model. At step 508 of FIG. 5, a data tagging step is performed for time synchronization of values of the sound velocity information, and the concentration of the one or more fluids. Further, as depicted in step 510 of FIG. 5, the temperature of the mixed fluid chamber is estimated using the stand-alone AI based model for a plurality of test input data.

The method of the present disclosure provides accurate measurement of average temperature of the mixed fluid chamber that contains mixture of different compositions with and without knowledge of fluid flow. Also, the proposed method helps in continuous monitoring of temperature by providing continuous feedback for process monitoring.

The illustrated steps of method 300 is set out to explain the exemplary embodiments shown, and it should be anticipated that ongoing technological development may change the manner in which particular functions are performed. These examples are presented herein for purposes of illustration, and not limitation.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
receiving, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber;
determining, one or more fluid parameters using one of (i) a bernoulli principle based fluid model or (ii) a state space based fluid model;
determining, an information pertaining to a plurality of thermocouples comprised in the mixed fluid chamber, wherein the information includes corresponding location coordinates of the plurality of thermocouples and temperature measured at the corresponding location coordinates of the plurality of thermocouples;
generating, ground truth temperature data for the mixed fluid chamber using a gradient based heat diffusion model based on the information pertaining to each of the plurality of thermocouples;
training an artificial intelligence (AI) based model using the one or more fluid parameters, the generated ground truth temperature data, and the sound velocity information; and
estimating, for a plurality of test input data, temperature of the mixed fluid chamber using the trained AI based model.

2. The method of claim 1, wherein a plurality of acoustic transmitter and receiver pairs are used in the mixed fluid chamber to provide the sound velocity information determined using the acoustic pyrometer based technique.

3. The method of claim 2, wherein inherent drift and noise is reduced by using the plurality of acoustic transmitter and receiver pairs.

4. The method of claim 1, wherein the one or more fluid parameters determined using the bernoulli principle based fluid model include spatio-temporal variation in concentration of the one or more fluids present in close proximity of the one or more chemical sensors in the mixed fluid chamber.

5. The method of claim 1, wherein the state space based fluid model is implemented using a Kalman filter or an extended Kalman filter.

6. The method of claim 1, wherein the ground truth temperature data is indicative of spatio-temporal variation of temperature of the one or more fluids inside the mixed fluid chamber.

7. The method of claim 1, further comprising training the artificial intelligence (AI) based model to function as a stand-alone model without using the one or more fluid parameters determined by the bernoulli principle based fluid model or the state space based fluid model.

8. A system, comprising:
a memory;
one or more communication interfaces; and
one or more hardware processors coupled to said memory through said one or more communication interfaces, wherein said one or more hardware processors are configured to:
receive, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber;
determine, one or more fluid parameters using one of (i) a bernoulli principle based fluid model or (ii) a state space based fluid model;
determine, an information pertaining to a plurality of thermocouples comprised in the mixed fluid chamber, wherein the information includes corresponding location coordinates of the plurality of thermocouples and temperature measured at the corresponding location coordinates of the plurality of thermocouples;
generate, ground truth temperature data for the mixed fluid chamber using a gradient based heat diffusion model based on the information pertaining to each of the plurality of thermocouples;
train, an artificial intelligence (AI) based model using the one or more fluid parameters, the generated ground truth temperature data, and the sound velocity information; and
estimate, for a plurality of test input data, temperature of the mixed fluid chamber using the trained AI based model.

9. The system of claim 8, wherein a plurality of acoustic transmitter and receiver pairs are used in the mixed fluid chamber to provide the sound velocity information determined using the acoustic pyrometer based technique.

10. The system of claim 9, wherein inherent drift and noise is reduced by using the plurality of acoustic transmitter and receiver pairs.

11. The system of claim 8, wherein the one or more fluid parameters determined using the bernoulli principle based fluid model include spatio-temporal variation in concentration of the one or more fluids present near the one or more chemical sensors in the mixed fluid chamber.

12. The system of claim 8, wherein the state space based fluid model is implemented using a Kalman filter or an extended Kalman filter.

13. The system of claim 8, wherein the ground truth temperature data is indicative of spatio-temporal variation of temperature of the one or more fluids inside the mixed fluid chamber.

14. The system of claim 8, further comprising training the artificial intelligence (AI) based model to function as a stand-alone model without using the one or more fluid parameters determined by the bernoulli principle based fluid model or the state space based fluid model.

15. One or more non-transitory machine-readable information storage mediums comprising one or more instructions which when executed by one or more hardware processors cause:
receiving, a plurality of input data pertaining to a mixed fluid chamber, wherein the plurality of input data includes (i) sound velocity information determined using an acoustic pyrometer based technique, (ii) location information of one or more chemical sensors deployed in the mixed fluid chamber, (iii) concentration of one or more fluids determined using the one or more chemical sensors and (iv) dimension of the mixed fluid chamber;

determining, one or more fluid parameters using one of (i) a bernoulli principle based fluid model or (ii) a state space based fluid model;

determining, an information pertaining to a plurality of thermocouples comprised in the mixed fluid chamber, wherein the information includes corresponding location coordinates of the plurality of thermocouples and temperature measured at the corresponding location coordinates of the plurality of thermocouples;

generating, ground truth temperature data for the mixed fluid chamber using a gradient based heat diffusion model based on the information pertaining to each of the plurality of thermocouples;

training an artificial intelligence (AI) based model using the one or more fluid parameters, the generated ground truth temperature data, and the sound velocity information; and estimating, for a plurality of test input data, temperature of the mixed fluid chamber using the trained AI based model.

* * * * *